(12) United States Patent
Tang et al.

(10) Patent No.: US 12,171,957 B2
(45) Date of Patent: Dec. 24, 2024

(54) STEERABLE GUIDING SHEATH WITH RACK AND PINION DEFLECTION MECHANISM

(71) Applicant: Biosense Webster (Israel) Ltd., Yokneam (IL)

(72) Inventors: Raymond Yue-Sing Tang, Rosemead, CA (US); Eric E. Bielefeld, Floyds Knobs, IN (US); John Miser, Crestwood, KY (US); Brian Raze, Yorba Linda, CA (US)

(73) Assignee: Biosense Webster (Israel) Ltd. (IL)

( * ) Notice: Subject to any disclaimer, the term of this patent is extended or adjusted under 35 U.S.C. 154(b) by 688 days.

(21) Appl. No.: 16/877,363

(22) Filed: May 18, 2020

(65) Prior Publication Data

US 2020/0276415 A1     Sep. 3, 2020

Related U.S. Application Data

(63) Continuation of application No. 15/372,329, filed on Dec. 7, 2016, now Pat. No. 10,653,860.

(51) Int. Cl.
*A61M 25/01*     (2006.01)
*A61B 5/00*      (2006.01)
(Continued)

(52) U.S. Cl.
CPC ....... *A61M 25/0136* (2013.01); *A61B 5/6852* (2013.01); *A61M 25/0147* (2013.01);
(Continued)

(58) Field of Classification Search
CPC .......... A61M 25/0136; A61M 25/0147; A61M 25/0133; A61M 25/0105; A61M 2205/58;
(Continued)

(56) References Cited

U.S. PATENT DOCUMENTS 4,757,827 A * 7/1988 Buchbinder ...... A61M 25/0136
                                                    604/170.01
5,364,352 A   11/1994 Cimino et al.
(Continued)

FOREIGN PATENT DOCUMENTS

CN     101106945 A     1/2008
CN     104883945 A     6/2018
(Continued)

OTHER PUBLICATIONS

European Patent Office Search Report for Application No. EP 17205691.3, dated Apr. 24, 2018. 9 pages.
(Continued)

*Primary Examiner* — Nilay J Shah
(74) *Attorney, Agent, or Firm* — Frost Brown Todd LLP

(57) ABSTRACT

A guiding sheath has a braided layer for improved deflection characteristics and ring electrodes for electrical sensing, mapping and visualization, wherein lead wires for the ring electrodes are passed through lumened tubing position under the braided layer in a proximal portion of the guiding sheath shaft and above the braided layer in a distal portion of the guiding sheath shaft. Moreover, the hemostatic valve includes an improved friction ring with air vents to reduce the risk of air being introduced into the valve.

20 Claims, 7 Drawing Sheets

(51) Int. Cl.
*A61M 39/06* (2006.01)
*A61M 39/22* (2006.01)
*A61B 17/00* (2006.01)

(52) U.S. Cl.
CPC .......... *A61M 39/06* (2013.01); *A61M 39/223* (2013.01); *A61B 5/6876* (2013.01); *A61B 2017/00318* (2013.01); *A61M 25/0133* (2013.01); *A61M 2039/062* (2013.01); *A61M 2039/229* (2013.01); *A61M 2205/581* (2013.01)

(58) Field of Classification Search
CPC ...... A61M 2205/581; A61M 2205/582; A61M 39/06; A61M 39/223
See application file for complete search history.

(56) References Cited

U.S. PATENT DOCUMENTS

| | | | |
|---|---|---|---|
| 5,833,604 | A | 11/1998 | Houser et al. |
| 6,183,463 | B1 | 2/2001 | Webster, Jr. |
| 9,498,602 | B2 | 11/2016 | Osypka |
| 10,653,860 | B2 | 5/2020 | Tang |
| 2006/0142694 | A1 | 6/2006 | Bednarek et al. |
| 2013/0184642 | A1* | 7/2013 | O'Donnell ........ A61M 25/0147 604/95.04 |
| 2014/0100445 | A1* | 4/2014 | Stenzel ................ G01R 33/287 600/417 |
| 2015/0105655 | A1 | 4/2015 | Tegg et al. |
| 2015/0196736 | A1 | 7/2015 | Tegg |
| 2015/0335861 | A1 | 11/2015 | Osypka et al. |
| 2016/0058975 | A1 | 3/2016 | Kimmel et al. |
| 2016/0074625 | A1 | 3/2016 | Furnish |
| 2016/0206853 | A1 | 7/2016 | Boldue et al. |

FOREIGN PATENT DOCUMENTS

| | | |
|---|---|---|
| EP | 033283 B1 | 1/1993 |
| EP | 1 050 316 A1 | 11/2000 |
| JP | 2006-187606 A | 7/2006 |
| WO | WO 2013/096676 A1 | 6/2013 |

OTHER PUBLICATIONS

First Office Action for Chinese Application No. 201711281791, dated Mar. 19, 2021, 9 pages and English Translation, 11 pages.
Second Office Action for Chinese Application No. 201711281791, dated Aug. 20, 2021, 4 pages and English Translation, 3 pages.
Third Office Action for Chinese Application No. 201711281791, dated Jan. 29, 2022, 6 pages, and English Translation, 9 pages.
English Translation of First Search Report for Chinese Application No. 201711281791, dated Mar. 1, 2021, 3 pages.
English Translation of Notification of Reasons for Refusal for Japanese Application No. 2017-234022, dated Jun. 15, 2021, 4 pages.
English Translation of Notification of Reasons for Refusal for Japanese Application No. 2017-234022, dated Feb. 15, 2022, 4 pages.
JPO Search Report dated Apr. 22, 2021, issued in corresponding JP Patent Application No. 2017-234022, English translation, 16 pages.
Japanese Notification of Reasons for Refusal dated Sep. 5, 2023, for Application No. 2022-179442, 3 pages.

\* cited by examiner

STEERABLE GUIDING SHEATH WITH RACK AND PINION DEFLECTION MECHANISM

CROSS-REFERENCE TO RELATED APPLICATION(S)

This application is a continuation of and claims priority to and the benefit of U.S. patent application Ser. No. 15/372,329 filed Dec. 7, 2016, now U.S. Pat. No. 10,653,860, the entire content of which is incorporated herein by reference.

FIELD OF INVENTION

This invention relates to a guiding sheath which is especially suitable for guiding electrophysiology catheter, in particular, a deflectable guiding sheath.

BACKGROUND

Guiding sheaths are well known for use in facilitating pathway for a treatment or diagnostic catheter. Catheterization of the human heart often necessitates having a catheter gain access to the heart chambers, via a femoral vein and the aorta. To provide variation in movement, guiding sheaths (much like the catheters that are passed through the guiding sheaths) may be steerable or deflectable with the use of one or more puller wires for improved maneuverability in the patient's vasculature.

Accordingly, there is a desire for a guiding sheath with improved deflection characteristics and smoother operation in deflection mechanisms of the control handle.

SUMMARY OF THE INVENTION

In some embodiments, a guiding sheath assembly comprises an elongated shaft and a control handle proximal of the shaft, the control handle having a longitudinal axis. The control handle includes a rotatable shaft, a pinion, and first and second shuttles. The shaft is configured for rotation about the longitudinal axis. The first shuttle configured for translation along the longitudinal axis in one direction in response to rotation of the rotatable shaft, wherein the first shuttle has a first plurality of teeth. The opinion is in engagement with the first plurality of teeth, and configured for rotation about an axis generally perpendicular to the longitudinal axis in response to the translation of the first shuttle. The second shuttle has a second plurality of teeth in engagement with the pinion and is configured for translation along the longitudinal axis in another direction opposite to the one direction in response to rotation of the pinion. The guiding sheath assembly also has a first puller wire extending along one side of the shaft and having a proximal end portion responsive to at least translation of the first shuttle in a proximal direction, and a second puller wire extending along another side of the shaft and having a proximal end portion response to at least translation of the second shuttle in the proximal direction.

In some embodiments, the control handle includes a control knob and the rotatable shaft being configured for rotation in response to rotation of the control knob.

In some embodiments, the rotatable shaft has an inner passage configured to receive a first distal portion of the first shuttle and a second distal portion of the second shuttle.

In some embodiments, the first and second distal portions are configured to form a cylindrical form when the first and second shuttles are laterally even with each other along the longitudinal axis.

In some embodiments, an inner surface of the inner passage is threaded and an outer surface of the first distal portion is threaded and engaged with the inner surface.

In some embodiments, the rotational shaft is rotationally and translationally coupled to the control knob.

In some embodiments, the rotational shaft is rotationally coupled to the control knob by a longitudinal ridge formed on an outer surface of the shaft.

In some embodiments, the rotational shaft is rotationally coupled to the control knob by a pin extending through a portion of the control knob and slot formed in the rotational shaft.

In some embodiments, the rotational shaft is rotationally and translationally coupled to the control knob at its distal end.

In some embodiments, the control handle includes a neutral indicator.

In some embodiments, the neutral indicator includes a first member on the first shuttle and a second member on the second shuttle, wherein the first and second members are configured for releasable engagement.

In some embodiments, the neutral indicator is configured to provide resistance to disengagement and re-engagement.

In some embodiments, the first neutral indicator includes a tapered projection, and the second neutral indicator includes a tapered recess.

In some embodiments, a guiding sheath assembly comprises an elongated shaft, and a control handle proximal of the shaft. The control handle has a longitudinal axis, and includes a control knob configured for rotation about the longitudinal axis, and a hollow rotatable shaft configured for rotation about the longitudinal axis in response to rotation of the control knob. The control handle also includes a first shuttle configured for translation along the longitudinal axis in one direction in response to rotation of the rotatable shaft, the first shuttle having a first plurality of teeth, a pinion in engagement with the first plurality of teeth, the pinion configured for rotation about an axis generally perpendicular to the longitudinal axis in response to the translation of the first shuttle, and a second shuttle having a second plurality of teeth in engagement with the pinion, the second shuttle configured for translation along the longitudinal axis in another direction opposite to the one direction in response to rotation of the pinion. The guiding sheath assembly further has a first puller wire extending along one side of the shaft and having a proximal end portion responsive to at least translation of the first shuttle in a proximal direction, and a second puller wire extending along another side of the shaft and having a proximal end portion response to at least translation of the second shuttle in the proximal direction.

In some embodiments, a control handle for use in controlling deflection of a medical guiding sheath shaft, includes a control knob configured for rotation about a longitudinal axis of the control handle, and a hollow rotatable shaft configured for rotation about the longitudinal axis in response to rotation of the control knob. The control handle also includes a first shuttle configured for translation along the longitudinal axis in one direction in response to rotation of the rotatable shaft, wherein the first shuttle has a first plurality of teeth. The control handle further includes a pinion in engagement with the first plurality of teeth, wherein the pinion is configured for rotation about an axis generally perpendicular to the longitudinal axis in response to the translation of the first shuttle. The control handle also includes a second shuttle having a second plurality of teeth in engagement with the pinion, the second shuttle configured for translation along the longitudinal axis in another direction opposite to the one direction in response to rotation of the pinion, wherein the first and second shuttles are configured to respectively act first and second puller wires extending along the guiding sheath shaft.

In some embodiments, distal ends of the first and second shuttles extend into a proximal portion of the rotatable shaft.

In some embodiments, an inner surface of the rotatable shaft is threaded and an outer surface of the first shuttle is threaded for rotationally coupling the rotatable shaft and the first shuttle.

In some embodiments, the first shuttle is directly responsive to rotation of the rotatable shaft and the second shuttle is directly responsive to rotation of the pinion.

BRIEF DESCRIPTION OF THE DRAWINGS

These and other features and advantages of the present invention will be better understood by reference to the following detailed description when considered in conjunction with the accompanying drawings. It is understood that selected structures and features have not been shown in certain drawings so as to provide better viewing of the remaining structures and features.

DETAILED DESCRIPTION OF THE INVENTION

Figure 1:
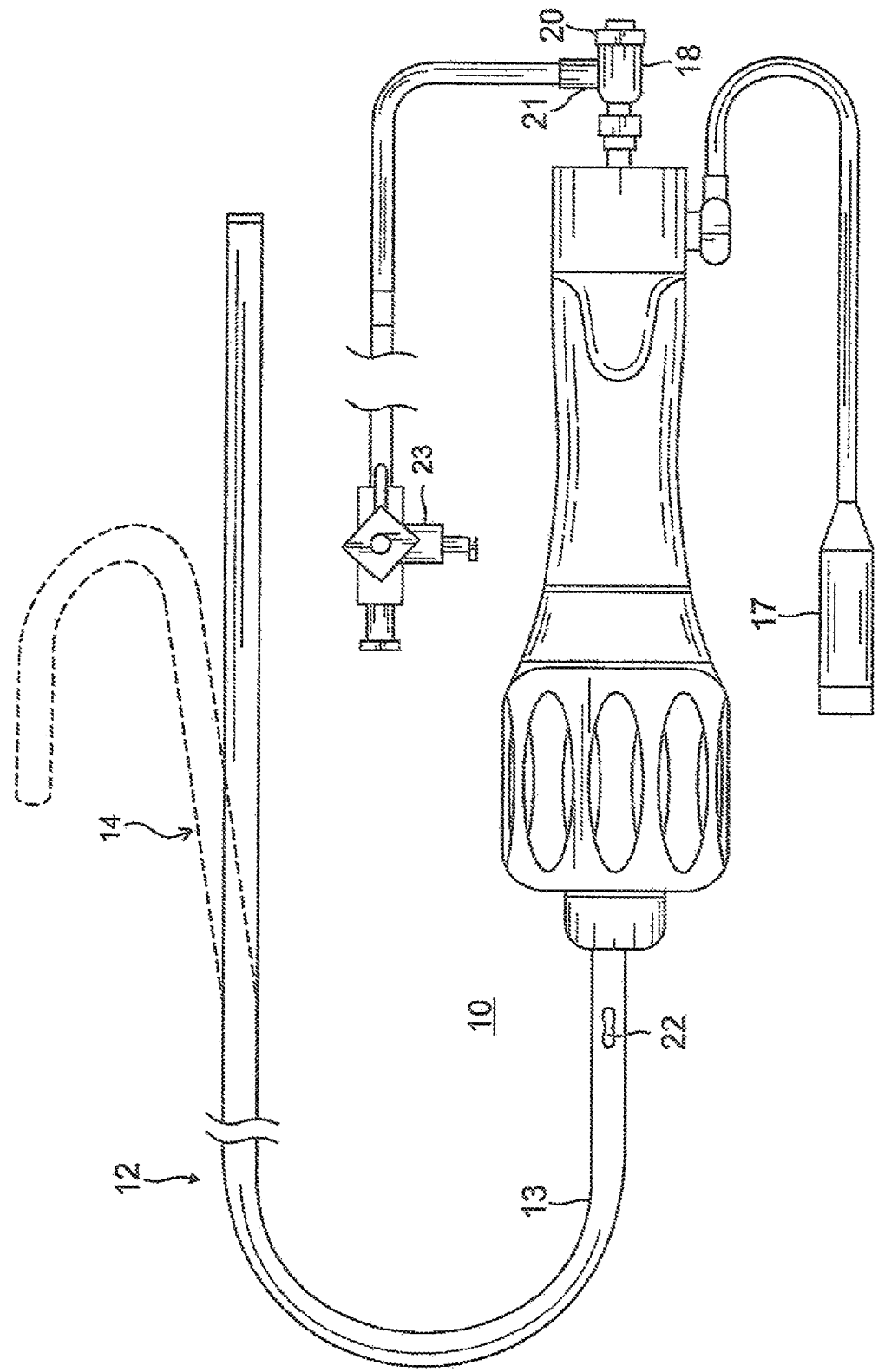
FIG. 1 is a top plan view of a guiding sheath including a control handle, in accordance with an embodiment of the present invention.

Referring to FIG. 1, in some embodiment embodiments of present invention, a guiding sheath assembly 10 includes an elongated and flexible sheath 12, and a control handle 16 proximal of sheath 12. The sheath 12 includes a proximal section 13 and a distal deflection section 14. The control handle 16 may be connected to an electrical connector 17 for transmitting electrical signals, as sensed by one or more ring electrodes carried on the sheath 12, including, for example, the deflection section 14. Also attached to the control handle 16, as shown in FIG. 1, is a hemostatic valve 18 adapted to receive a catheter (not shown) that can be advanced through a center lumen 22 of the guiding sheath assembly 10 (FIG. 1). The hemostatic valve 18 also has side port 21 terminating in a luer hub, such as a two-way stop cock 23, for connection to one or more fluid sources (not shown) for providing fluid into and through the lumen 22 of the guiding sheath assembly 10.

Figure 2:
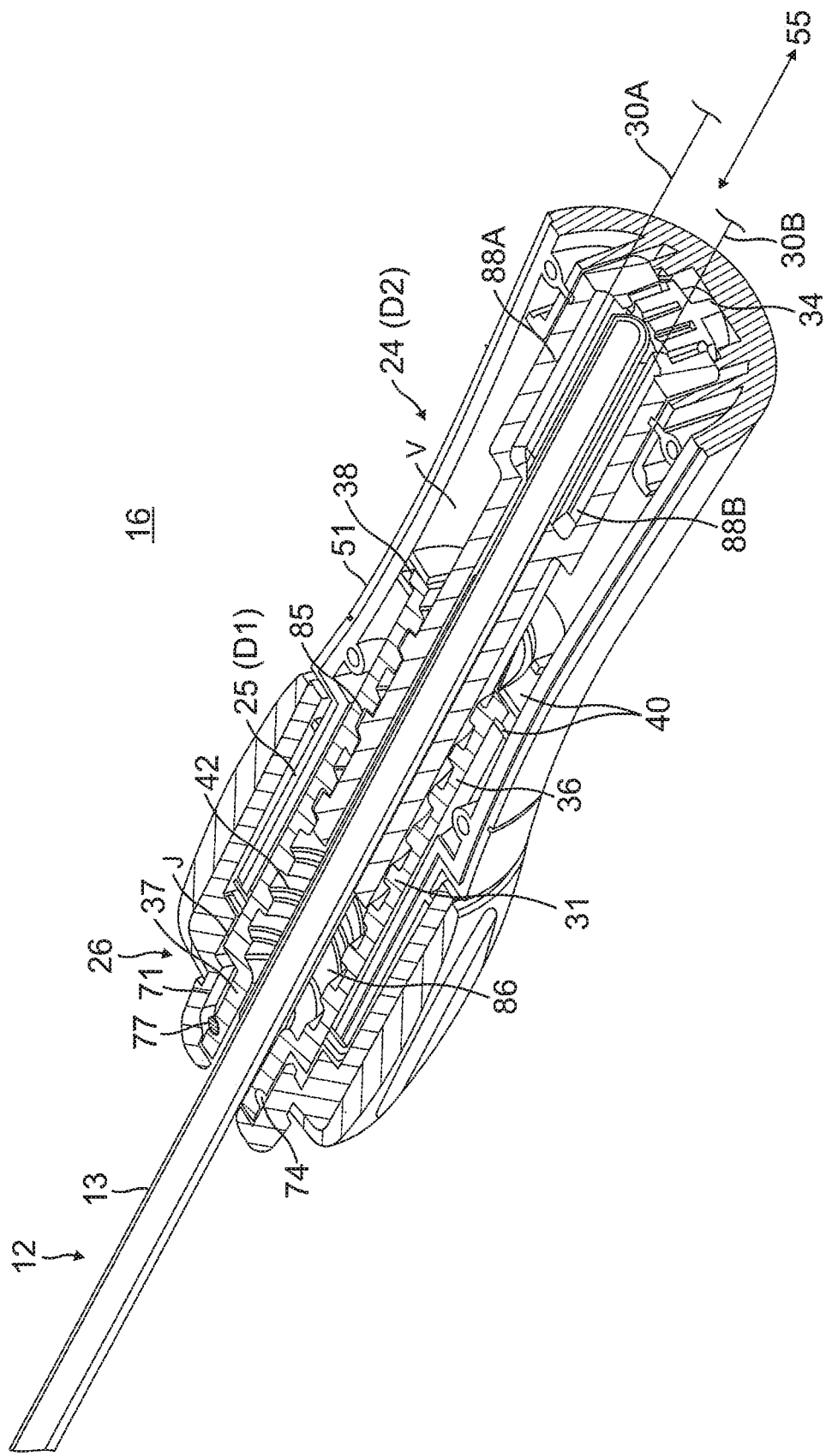
FIG. 2 is a longitudinal cross-sectional view of a control handle of FIG. 1.
Figure 3:
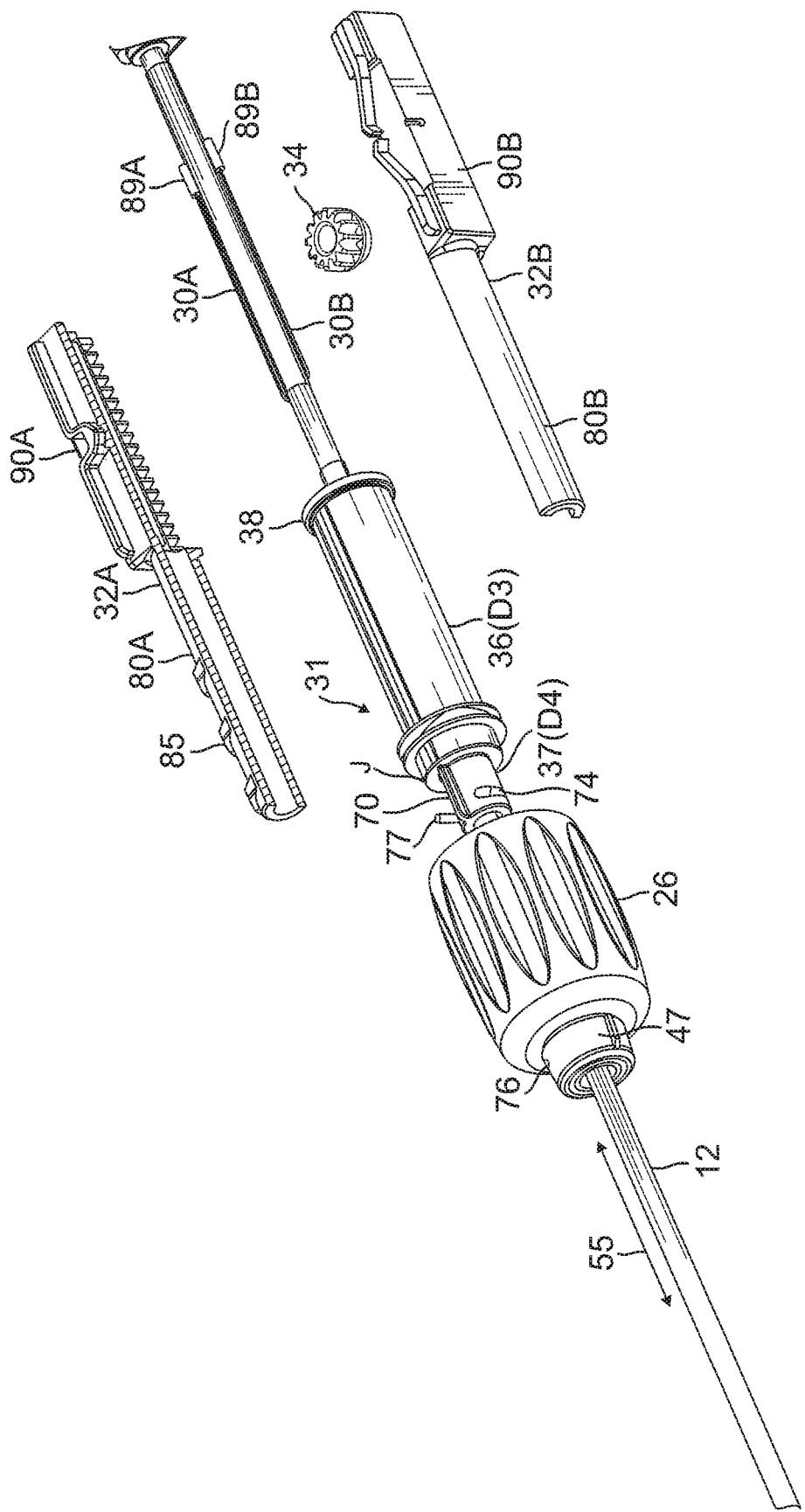
FIG. 3 is an exploded view of the control handle of FIG. 1, with a housing removed.

As shown in FIG. 2 and FIG. 3, the control handle 16 includes an elongated, generally cylindrical main body 24 with a narrower distal portion or stem 25, and a distal rotational control knob 26 mounted on the distal portion stem 25. The main body 24 has an outer shell-half member formed to define an interior volume V and whose edges 51 meet along a longitudinal seam. The distal stem 25 of the main body has a smaller outer diameter D1 compared to the outer diameter D2 of a proximal portion of the main body 24. The control knob 26 is configured for rotation by a user's thumb and forefinger when the user is grasping the main body 24 of the control handle 16. To enable deflection of the deflection section 14 of the guiding sheath 12 via first and second puller wires 30A and 30B, the control handle 16 includes in its interior volume V a rotatable shaft 31, first and second shuttles 32A and 32B, and a pinion 34. The rotatable shaft 31 is responsive to the control knob 26 in driving first shuttle 32A to move linearly along a longitudinal axis 55 in a first direction, and the pinion 34 couples the second shuttle 32B to the first shuttle 32A such that the second shuttle 32B moves linearly along the longitudinal axis in a second direction opposition to the first direction. With proximal ends of the first and second puller wires 30A and 30B anchored, or at least coupled, to the first and second shuttles 32A and 32B, respectively, such coupled and opposite translational movement of the first and second shuttles actuate the first and second puller wires for bi-directional deflection of the deflection section 14 of the guiding sheath 12.

The rotatable shaft 31 has a main proximal section 36 with an outer diameter D3, a shorter distal section 37 with an outer diameter D4, and a step junction J therebetween between sections 36 and 37. In the illustrated embodiment, the diameter D3 is greater than the diameter D4, but it is understood that the two diameters may be generally equal or the diameter D4 may be greater than the diameter D3. As better seen in FIG. 2, the rotatable shaft 31 is situated relative to main body 24 of the control handle 16 such that its proximal section 36 extends through both the main body 24 and the distal stem 25 of the control handle 16 and past a distal end of the distal stem 25, with the junction J and the distal section 37 being distal of the distal stem 25 of the main body 24 so that the distal section 37 is not surrounded by the distal stem 25. The rotatable shaft 31 is connected and affixed at its proximal end to the main body 24 by a proximal outer circumferential lip 38 that engages with an inner circumferential slot defined between circumferential flanges 40 formed in the interior volume V of the main body 24.

Figure 4:
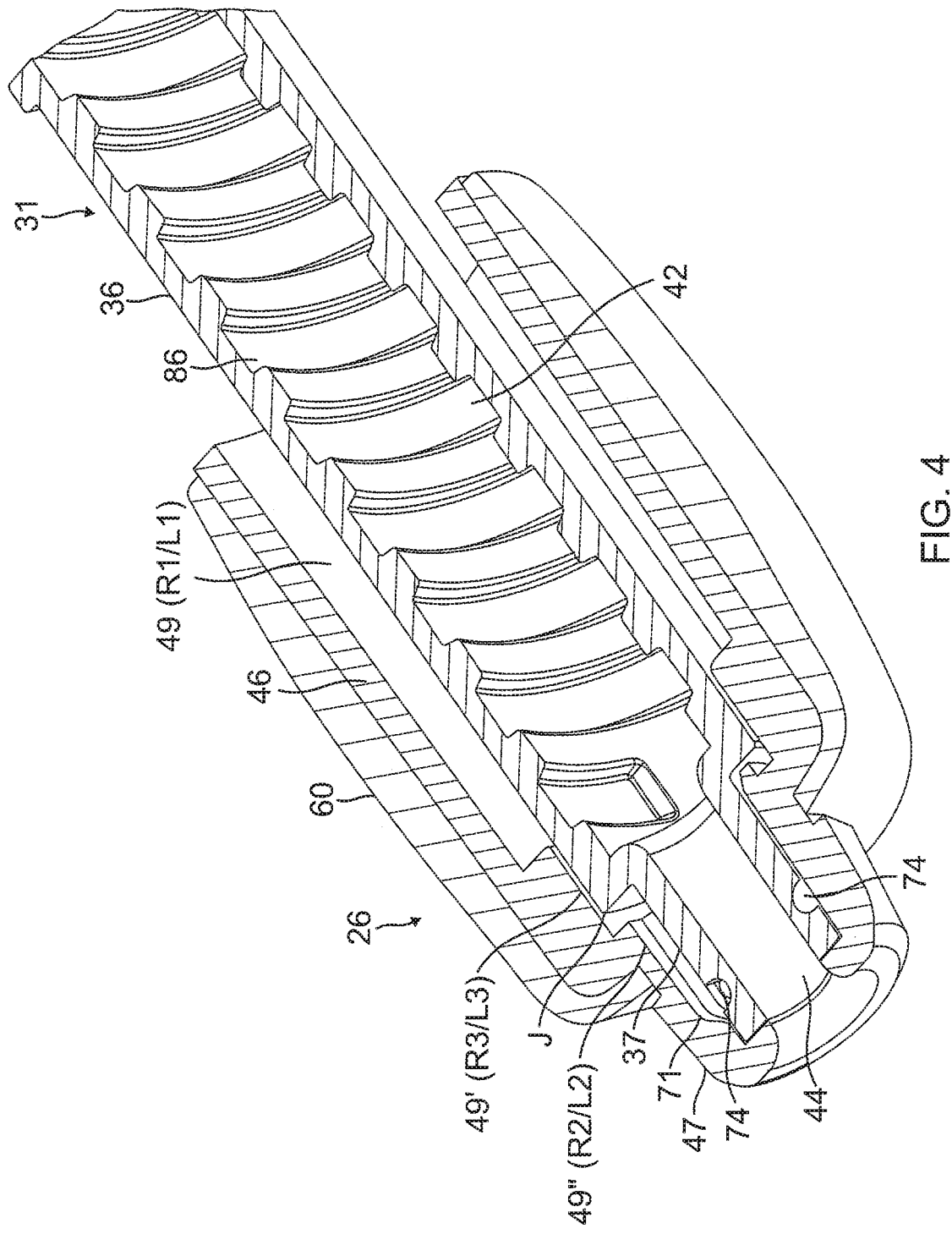
FIG. 4 is a longitudinal cross-sectional view of a distal portion of the control handle of FIG. 1, including a control knob.

With reference to FIG. 4, the rotatable shaft 31 is hollow having an interior passage 42. The passage 42 is in communication with a distal inlet 44 whose diameter is merely slightly greater than the diameter of the guiding sheath 12. The passage 42 is threaded and has a diameter to accommodate both the guiding sheath 12 and the shuttles 32A and 32B circumferentially surrounding the guiding sheath 12, as discussed below in further detail.

The control knob 26, which is mounted on the distal stem 25 of the main body 24 of the control handle 16 and the rotatable shaft 31, has a main proximal portion 46 and a short distal end portion 47. The control knob 26 is generally cylindrical with a longitudinal hollow interior that extends through its entire length. The hollow interior has a main proximal section 49, a mid-section 49' and a distal section 49". The main proximal section 49 of the hollow interior is defined by a greater first radius R1 and a greater first length L1 to accommodate and circumferentially surround the guiding sheath 12 and the shuttles 32A and 32B. The distal section 49" of the hollow interior is defined by a lesser second radius R2, where R1>R2, and a shorter second length L2, where L1>L2, to accommodate and circumferentially surround the guiding sheath 12 and the distal section 37 of the rotatable shaft 31. The mid-section 49' of the hollow interior is defined by a third radius R3, where R1>R3>R2, and a third length L3, where L1>L3, to accommodate and circumferentially surround the guiding sheath 12 and the junction J of the rotatable shaft 31. A friction-inducing cover 60 may be mounted on an outer surface of the control knob 26 for the user's ease and comfort in manipulating and rotating the control knob relative to the main body 24 of the control handle 16.

To rotationally couple the rotatable shaft 31 to the control knob 26 (for common rotational movement of the rotatable shaft 31 and control knob 26), an outer surface of the distal section of the shaft has a longitudinal ridge 70 (FIG. 3) that is received in and engages with a corresponding longitudinal recess 71 (FIG. 4) formed an inner surface defining the hollow interior 49" of the control knob 26. To translationally affix the control knob 26 to the rotatable shaft 31 (for common translational movement of the control knob 26 and rotatable shaft 31) and hence the main body 24, the outer surface of the shaft 31 also has one or more linear slots 74 oriented perpendicularly to the longitudinal axis of the rotatable shaft 31. Each slot 74 is aligned with a respective hole 76 (FIG. 5) formed through a side of the distal end portion 47 of the control knob 26, so that a respective pin 77 may be inserted into the hole 76 and the slot 74 to couple the control knob 26 and the rotatable shaft 31 for common translational movement.

It is understood that other embodiments of the guiding sheath assembly may provide a rotatable shaft 31 with an exposed portion for direct manipulation by a user, without the control knob 26.

Figure 5:
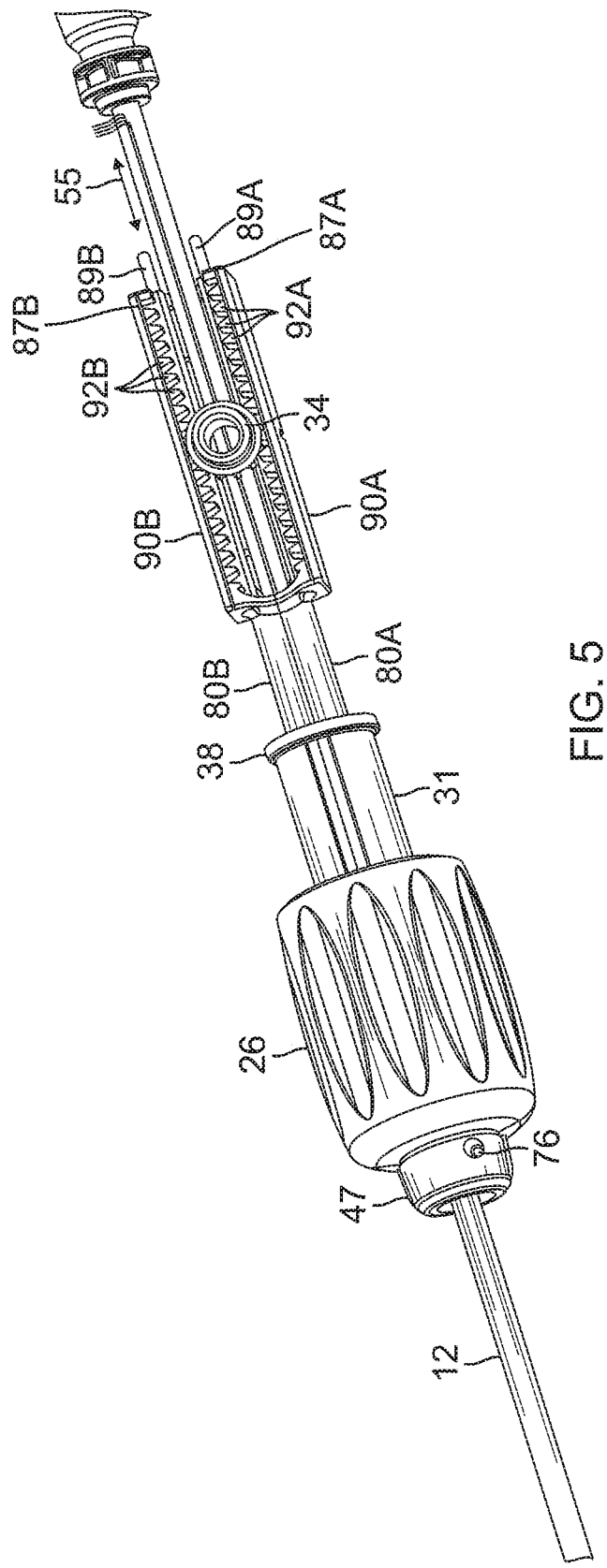
FIG. 5 is a perspective view of the control handle of FIG. 1, with the housing removed.

As shown in FIG. 3 and FIG. 5, the shuttles 32A and 32B have a similar construction to each other, with the understanding that each is generally a mirror image of the other, although the first shuttle 32A is driven by the rotatable shaft 31 and second shuttle 32B is driven by the first shuttle 32A via the pinion 34 situated between them. Each shuttle 32A and 32B has a respective elongated body having a distal portion 80A and 80B with a C-shaped end cross-section, and a respective proximal rack portion 90A and 90B with a respective plurality of teeth 92A and 92B arranged longitudinally. The first and second shuttles are arranged to face each other and engage the pinion 34 such that the distal portions 80A and 80BC together can form a cylindrical form with an outer circumferential surface that fits within the threaded passage 42, and an inner circumferential surface that defines a passage 93 for the guiding sheath 12 to pass through. As shown in FIG. 5, the rack portion 90A and 90B of each shuttle faces each other with the pinion 34 in between so that the teeth 92A and 92B of each rack portion can engage with teeth of the pinion 34 which is mounted for rotation about an axis perpendicular to the longitudinal axis 55 of the control handle 16.

With reference to FIG. 2 and FIG. 3, an outer surface of the distal portion 80A of the first shuttle 32A is configured with an external or male threaded surface 85. An inner circumferential surface of the rotatable shaft 31 is configured with an internal or female threaded surface 86 (FIG. 4) which receives the male threaded surface 85 of the first shuttle 32A for coupling the first shuttle 32A and the rotatable shaft 31 in converting rotational movement of the rotatable shaft 31 into translation movement of the first shuttle 32A. In contrast, the outer surface of the distal portion 80B of the second shuttle 32B is smooth, without any feature engaging the threaded female surface of the rotatable, so that it can move independently of the threaded male surface 85. Accordingly, as a user rotates the control knob 26 in a first direction, the rotatable shaft 31 which is rotationally coupled to the control knob 26 (for common rotational movement) via the longitudinal ridge 70 also rotates. With the rotatable shaft 31 rotationally and translationally locked to the control knob 26 (for common rotational and common translational movement) via the longitudinal ridge 70 and the one or more pins 77, rotation of the shaft 31 drives the first shuttle 32A to translate along the longitudinal axis in a first direction (for example, proximally). As the first shuttle 32A translates, its teeth 92A drive the pinion 34 to rotate in a first direction (for example, clockwise), which in turn drives the second shuttle 32B to translate along the longitudinal axis 55 in a second direction opposite of the first direction (for example, distally). So arranged, the male and female threaded surfaces 85 and 86 convert rotational movement of the control knob 26 into linear movement of the shuttles 32A and 32B. With proximal ends of the first and second puller wires 30A and 30B anchored, coupled or otherwise responsive to the first and second shuttles 32A and 32B, respectively, linear and opposite movements of the shuttles actuate the puller wires for bi-directional deflection of the deflection section 14 of the guiding sheath 12. In the illustrated embodiment, the proximal ends of the puller wires 30A and 30B are coupled to the rack portions 90A and 90B of the shuttles 32A and 32B, respectively. Thus, when one puller wire is drawn proximally under tension by its respective shuttle, the other puller wire is simultaneously released from tension by its respective shuttle moving distally.

As shown in FIG. 2, a proximal end segment of each puller wire 30A and 30B extends outside of the sheath 12, in a respective longitudinal channel 88A and 88B formed in the proximal rack portion 90A and 90B of each shuttle 32A and 32B. As shown in FIG. 5, a stop 89A and 89B, for example, a hypotube, is affixed to the proximal end of each puller wire 30A and 30B, and the stop is positioned proximal of a proximal end 87A and 87B of the respective rack portion 90A and 90B so that the rack portion can push or otherwise act on the stop 89A and 89B, respectively, to draw the puller wire 30A and 30B proximally when the shuttle 32A and 32B is moved proximally. When a shuttle 32A and 32B is moved distally, the proximal end of the rack portion 90A and 90B comes out of contact with the stop 89A and 89B, releasing the puller wire 30A and 30B from tension. It is understood that the stop 89A and 89B may also be embedded or otherwise anchored to the rack portion or any part of the shuttle to effect deflection of the sheath.

Because the first and second shuttles 32A and 32B move in opposite directions along the longitudinal axis 55, an initial positioning of the shuttles relative to each other and to the passage 42 is made during assembly of the control handle. For example, as shown in FIG. 2, each shuttle is positioned in the passage 42 of the rotatable shaft 31 such that they are even with each other along the longitudinal axis 55, and each has a distal end positioned generally at midpoint along the passage 42 so that each shuttle has sufficient room to move correspondingly proximally or distally within the rotatable shaft 31. The stops 89A and 89B may be positioned relative to the shuttles such that there is minimal or even tension exerted on each puller wire 30A and 30B for a generally neutral guiding sheath with little, if any, deflection. So arranged, the shuttles adopt a "neutral" or initial configuration from which the user may evenly deflect the guiding sheath bi-directionally.

As shown in FIG. 5, the pinion 34 is positioned in between and relative to the shuttles 32A and 32B so that their teeth 92A and 92B remain engaged while the shuttles translate in response the user's manipulation of the control knob 26. In that regard, the length of the rack portions 90A and 90B are sufficiently long to ensure such continuous engagement.

It is understood that by changing one or more factors, including, for example, the length of the passage 42, the length of each distal portion 80A and 80B, the length of the rack portion 90A and 90B, the position of the pinion 34, and the number of pinions, different shuttle movement and deflection characteristics and limitations may be achieved, as needed or desired.

Figure 6A:
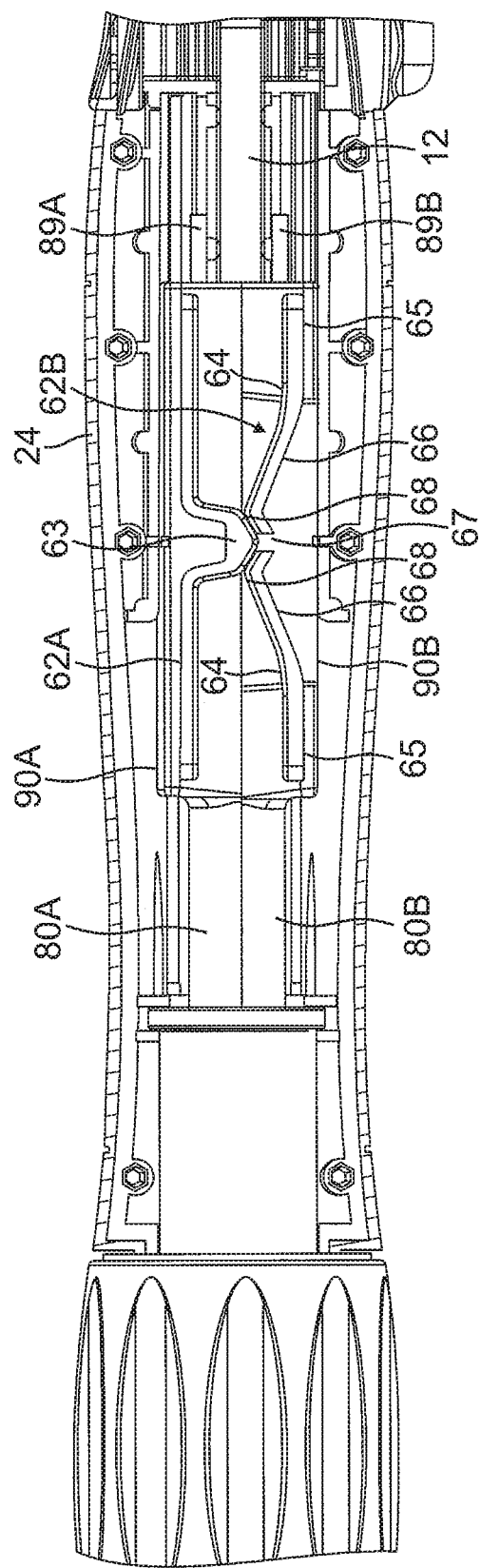
FIG. 6A is a top plan view of a neutral indicator with first and second members engaged, in accordance with one embodiment of the present invention.
Figure 6B:
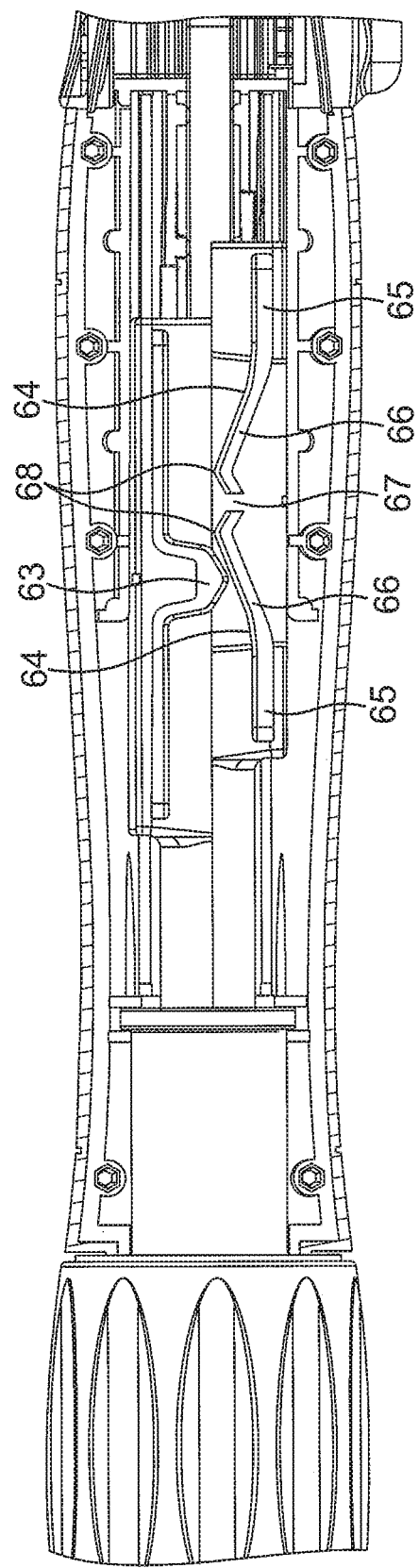
FIG. 6B is a top plan view of the neutral indicator of FIG. 6A with the first and second members disengaged.

With reference to FIG. 6A and FIG. 6B, an outer surface of each rack portion 90A and 90B, opposite of the teeth 92A and 92B, of each shuttle 32A and 32B is configured with a neutral indicator. The neutral indicator includes a first member 62A and a second member 62B configured for releasable engagement with each other to indicate a neutral position between the first and second shuttles 32A and 32B, that is, a relative position where the puller wires 30A and 30B are neutral and the guiding sheath 12 accordingly is generally straight, without deflection. In the illustrated embodiment, the first or male member 62A formed on the first shuttle 32A has a tapered projection 63 facing the second or female member 62B formed on the second shuttle 32B, which includes a pair of flexible guide rails 64 on either side, whose fixed ends 65 are affixed to the second shuttle 32B and whose free ends 66 are configured to jointly form a tapered recess 67 in which the tapered projection 63 nests when the shuttles 32A and 32B are in the neutral configuration.

Accordingly, the user is typically initially presented with the guiding sheath 12 undeflected where the first and second shuttles 32A and 32B are even with each other with the tapered projection 63 nesting in the tapered recess 67, as shown in FIG. 6A. When the user rotates the control knob 26 in one direction which drives the first and second shuttles 32A and 32B to translate in opposition directions, as shown in FIG. 6B, the tapered projection 63 disengages and moves out from the tapered recess 67 but only when the user rotates the control knob with sufficient force to flex the guide rails 64 and overcome the resistance presented by their angled ends 68. When the tapered projection 63 rides over and has moved past one of the angled ends 68, the guide rail 64 is sloped such that the resistance to movement of the tapered projection 63 decreases as the tapered projection 63 moves further away from the tapered recess 67. Thus, in rotating the control knob 26 to deflect the guiding sheath 12, the user experiences a greater or maximum resistance when the shuttles 32A and 32B initially move out of the neutral configuration, followed by increasing ease as the shuttles 32A and 32B translate in opposite directions. The control handle 16 may bear visual and/or tactile indicia to provide constant orientation of deflection direction. For example, clockwise rotation of the control knob 26 consistently deflects the shaft 12 toward the side or direction of the sideport 21, and counterclockwise rotation of the control knob 26 consistently deflects the shaft 12 toward an opposite side or direction.

Conversely, when releasing the deflection of the guiding sheath 12, the user rotates the control knob 26 in the opposite direction. As the shuttles 32A and 32B translate and approach each other and begin to laterally realign again, the tapered projection 63 and the tapered recess 67 approach each other and the user applies an increasing force to rotate the control knob 26 in order for the tapered projection 63 to ride back over the angled end 68 of a guide rail 64 before the tapered projection 63 can nest in the tapered recess 67. Accordingly, the increasing resistance posed by either of the sloped rails 64 and a greater or maximum resistance posed by an angled end 68 provides the user with a tactile feel or indication of when the tapered projection 63 is in the immediate proximity of the tapered recess 67. Engagement of the tapered projection 63 and the tapered recess 67 can provide the user with an audible "click" or signal when the flexible guide rail 64 snaps into its natural configuration when the tapered projection 63 no longer exerts any load on it.

The preceding description has been presented with reference to presently preferred embodiments of the invention. Workers skilled in the art and technology to which this invention pertains will appreciate that alterations and changes in the described structure may be practiced without meaningfully departing from the principal, spirit and scope of this invention. Any feature or structure disclosed in one embodiment may be incorporated in lieu of or in addition to other features of any other embodiments, as needed or appropriate. As understood by one of ordinary skill in the art, the drawings are not necessarily to scale. Accordingly, the foregoing description should not be read as pertaining only to the precise structures described and illustrated in the accompanying drawings, but rather should be read consistent with and as support to the following claims which are to have their fullest and fair scope.

What is claimed is:

1. A guiding sheath assembly, comprising:
   an elongated shaft;
   a control handle proximal of the elongated shaft, the control handle having a longitudinal axis, and including:
      a control handle housing;
      a hollow rotatable shaft inside the control handle housing and configured for rotation about the longitudinal axis of the control handle, the hollow rotatable shaft comprising an inner passage;
      a control knob coupled for common rotational movement to the hollow rotatable shaft;
      a first shuttle in rotational engagement with the hollow rotatable shaft and configured for translation along the longitudinal axis in one direction in response to rotation of the rotatable shaft, the first shuttle having a first rack portion comprising a first plurality of teeth;
      a pinion in engagement with the first plurality of teeth of the first shuttle, the pinion configured for rotation about an axis generally perpendicular to the longitudinal axis in response to the translation of the first shuttle; and
      a second shuttle having a second rack portion comprising a second plurality of teeth in engagement with the pinion, the second shuttle configured for translation along the longitudinal axis in another direction opposite to the one direction in response to rotation of the pinion, and both the first rack portion of the first shuttle and the second rack portion of the second shuttle remain outside the hollow rotatable shaft upon rotation of the rotatable shaft;
   the guiding sheath assembly further comprising:
   a first puller wire extending along one side of the elongated shaft and having a proximal end portion responsive to at least translation of the first shuttle in a proximal direction; and
   a second puller wire extending along another side of the elongated shaft and having a proximal end portion responsive to at least translation of the second shuttle in the proximal direction.

2. The guiding sheath assembly of claim 1, wherein a first distal portion of the first shuttle and a second distal portion of the second shuttle both extend into the inner passage of the hollow rotatable shaft, the first rack portion is at a proximal portion of the first shuttle, and the second rack portion is at a proximal portion of the second shuttle.

3. The guiding sheath assembly of claim 2, wherein the first and second distal portions are configured to form a generally cylindrical form when the first and second shuttles are laterally even with each other along the longitudinal axis.

4. The guiding sheath assembly of claim 2, wherein an inner surface of the inner passage of the hollow rotatable shaft and an outer surface of the first distal portion are in threaded engagement with each other.

5. The guiding sheath assembly of claim 1, wherein the hollow rotatable shaft and the control knob are fixed against axial translational movement along the longitudinal axis of the control handle.

6. The guiding sheath assembly of claim 1, wherein the hollow rotatable shaft is coupled for the common rotational movement to the control knob by a longitudinal ridge formed on an outer surface of the hollow rotatable shaft.

7. The guiding sheath assembly of claim 1, wherein the hollow rotatable shaft is coupled for the common rotational movement to the control knob by a pin extending through a portion of the control knob and a slot formed in the hollow rotatable shaft.

8. The guiding sheath assembly of claim 7, wherein the slot comprises a linear slot on the outer surface of the hollow rotatable shaft oriented generally perpendicular to a longitudinal axis of the hollow rotatable shaft, and the portion of the control knob through which the pin extends comprises a hole in
a side of the control knob, the hole in the side of the control knob being aligned with the slot on the outer surface of the hollow rotatable shaft.

9. The guiding sheath assembly of claim 1, wherein the hollow rotatable shaft is coupled for the common rotational movement to the control knob at a distal end of the hollow rotatable shaft.

10. The guiding sheath assembly of claim 1, wherein the control handle includes a neutral indicator.

11. The guiding sheath assembly of claim 10, wherein the neutral indicator includes a first member on the first shuttle and a second member on the second shuttle, the first and second members configured for releasable engagement.

12. The guiding sheath assembly of claim 11, wherein the neutral indicator is configured to provide resistance to disengagement and re-engagement.

13. The guiding sheath assembly of claim 11, wherein the first member of the neutral indicator includes a tapered projection, and the second member of the neutral indicator includes a tapered recess.

14. A guiding sheath assembly, comprising:
an elongated shaft;
a control handle proximal of the elongated shaft, the control handle having a longitudinal axis, and including:
a control handle housing;
a control knob configured for rotation about the longitudinal axis;
a hollow rotatable shaft inside the control handle housing and configured for rotation about the longitudinal axis in response to rotation of the control knob, the hollow rotatable shaft comprising an inner passage and being coupled for common rotational movement to the control knob;
a first shuttle in rotational engagement with the hollow rotatable shaft and configured for translation along the longitudinal axis in one direction in response to rotation of the hollow rotatable shaft, the first shuttle having a first rack portion comprising a first plurality of teeth;
a pinion in engagement with the first plurality of teeth of the first shuttle, the pinion configured for rotation about an axis generally perpendicular to the longitudinal axis in response to the translation of the first shuttle; and
a second shuttle having a second rack portion comprising a second plurality of teeth in engagement with the pinion, the second shuttle configured for translation along the longitudinal axis in another direction opposite to the one direction in response to rotation of the pinion, both the first rack portion of the first shuttle and the second rack portion of the second shuttle remaining outside the hollow rotatable shaft upon rotation of the rotatable shaft;
the guiding sheath assembly further comprising:
a first puller wire extending along one side of the elongated shaft and having a proximal end portion responsive to at least translation of the first shuttle in a proximal direction; and
a second puller wire extending along another side of the elongated shaft and having a proximal end portion responsive to at least translation of the second shuttle in the proximal direction.

15. The guiding sheath assembly of claim 14, wherein distal ends of the first and second shuttles extend into a proximal portion of the inner passage of the hollow rotatable shaft, the first rack portion is at a proximal portion of the first shuttle, and the second rack portion is at a proximal portion of the second shuttle.

16. The guiding sheath assembly of claim 15, wherein an inner surface of the hollow rotatable shaft and an outer surface of the first shuttle are in threaded engagement for coupling the hollow rotatable shaft and the first shuttle such that the first shuttle moves in response to rotation of the hollow rotatable shaft.

17. A control handle for use in controlling deflection of a medical guiding sheath shaft, the control handle having a longitudinal axis, and including:
a control handle housing;
a control knob configured for rotation about the longitudinal axis;
a hollow rotatable shaft inside the control handle housing and configured for rotation about the longitudinal axis in response to rotation of the control knob, the hollow rotatable shaft having an inner passage and being coupled for common rotational movement to the control knob;
a first shuttle in rotational engagement with the hollow rotatable shaft and configured for translation along the longitudinal axis in one direction in response to rotation of the hollow rotatable shaft, the first shuttle having a first rack portion comprising a first plurality of teeth;
a pinion in engagement with the first plurality of teeth of the first shuttle, the pinion configured for rotation about an axis generally perpendicular to the longitudinal axis in response to the translation of the first shuttle; and
a second shuttle having a second rack portion comprising a second plurality of teeth in engagement with the pinion, the second shuttle configured for translation along the longitudinal axis in another direction opposite to the one direction in response to rotation of the pinion, both the first rack portion of the first shuttle and the second rack portion of the second shuttle remaining outside the hollow rotatable shaft upon rotation of the rotatable shaft;

the first and second shuttles being configured to respectively act on first and second puller wires extending along the guiding sheath shaft.

18. The control handle of claim 17, wherein distal ends of the first and second shuttles extend into a proximal portion of the inner passage of the hollow rotatable shaft, the first rack portion is at a proximal portion of the first shuttle, and the second rack portion is at a proximal portion of the second shuttle.

19. The control handle of claim 18, wherein an inner surface of the hollow rotatable shaft and an outer surface of the first shuttle are in threaded engagement for coupling the hollow rotatable shaft and the first shuttle such that the first shuttle moves in response to rotation of the hollow rotatable shaft.

20. The control handle of claim 17, wherein the first shuttle is directly responsive to rotation of the hollow rotatable shaft and the second shuttle is directly responsive to rotation of the pinion.

* * * * *